United States Patent [19]
Robinson

[11] Patent Number: 5,763,766
[45] Date of Patent: Jun. 9, 1998

[54] VISCOMETER

[75] Inventor: Geoffrey Robinson, Spring, Tex.

[73] Assignee: Baker Hughes Incorporated, Houston, Tex.

[21] Appl. No.: 656,267

[22] PCT Filed: Dec. 17, 1993

[86] PCT No.: PCT/GB93/02575

§ 371 Date: Sep. 9, 1996

§ 102(e) Date: Sep. 9, 1996

[87] PCT Pub. No.: WO95/16905

PCT Pub. Date: Jun. 22, 1995

[51] Int. Cl.$^6$ .......................... G01N 33/48; G01N 11/14
[52] U.S. Cl. .......................... 73/54.33; 73/54.28
[58] Field of Search .................. 73/54.33, 54.28

[56] References Cited

U.S. PATENT DOCUMENTS

| | | | |
|---|---|---|---|
| 1,281,042 | 10/1918 | MacMichael | 73/54.33 |
| 2,354,299 | 7/1944 | Bays | 265/11 |
| 2,796,758 | 6/1957 | Meyers et al. | 73/60 |
| 2,957,339 | 10/1960 | Penny et al. | 73/59 |
| 3,292,422 | 12/1966 | Banks | 73/59 |
| 4,175,425 | 11/1979 | Brookfield | 73/59 |
| 4,347,734 | 9/1982 | Heinz | 73/59 |
| 4,448,061 | 5/1984 | Brookfield | 73/59 |
| 4,534,209 | 8/1985 | Sanders | 73/59 |
| 4,765,180 | 8/1988 | Clifton | 73/59 |
| 5,201,214 | 4/1993 | Sekiguchi et al. | 73/54.35 |
| 5,287,732 | 2/1994 | Sekiguchi | 73/54.33 |

FOREIGN PATENT DOCUMENTS

| | | |
|---|---|---|
| 0 018 905 A1 | 4/1980 | France. |
| 3531976 A1 | 9/1985 | Germany. |

*Primary Examiner*—Hezron E. Williams
*Assistant Examiner*—J. David Wiggins
*Attorney, Agent, or Firm*—Rosenblatt & Redano P.C.

[57] ABSTRACT

The invention comprises a viscometer which has a bob assembly unit suspended between the fixation points for a torsion wire. The torsion wire runs through a tube, which is connected to the bob. The tube has cutouts so that it may rotate in response to rotations of a cup, in which the bob is disposed. The framework that can include spokes or bars to support a fixation point for the wire is preferably positioned to extend through cutouts or open window-like slots in the tube so as not to interfere with rotational movements of the tube. An arm connected to the tube, in conjunction with a transducer, measures the angular deflection of the wire for determination of viscosity for the fluid being examined via a direct sensing means without any manual contact, visual observation or mental judgement by a test operator.

20 Claims, 1 Drawing Sheet

VISCOMETER

Priority is claimed under 35 U.S.C. §119(b) to PCT application No. PCT/GB93/02575, filed Dec. 17, 1993.

FIELD OF THE INVENTION

The field of this invention relates to viscometers, particularly those that require a high degree of accuracy.

BACKGROUND OF THE INVENTION

In prior designs for viscometers, a rotatably mounted container would hold the liquid whose viscosity is to be measured. A pendulum or a "bob" would be supported within the liquid on a wire and the cylinder holding the liquid would be rotated. The twisting force imparted to the wire holding the bob would then be measured. This twisting force would be used as the basis for measurement of the viscosity of the fluid at a particular temperature. Bobs of the prior designs were generally supported at a single point. These prior designs would use thin wire, ranging from 0.002 to 0.010 inches in diameter, in combination with heavy bobs to keep the bobs centered in the sample when the rotating cup is moving. Other designs involved rods in lieu of thin wires where the rods had a diameter greater than 0.125 inches. These designs lacked sensitivity because they required extreme forces to impart any twist to them. Yet, other designs, such as U.S. Pat. No. 4,299,118, employed rods in conjunction with a spring coupled to the drive through ball bearings. These types of connections had built-in inaccuracies because even with no sample in the rotating cup, a reading will be obtained when the drive is rotated simply due to frictional forces between the bob and the rotating cup. The thin wire systems were limited to water and low viscosity fluids. In the rod system, inaccuracies occurred because the detection and force-measuring devices were not necessarily linear for the sample in the speed range of interest and because of bearing friction due to the mechanical method of construction.

Prior viscometers of the types discussed above are illustrated in U.S. Pat. Nos. 3,435,666; 1,281,042; 1,192,861; 1,236,706; 2,203,132; 2,303,162; 2,398,574; 2,957,339; and 4,242,086; European Patent Application Nos. 384792; 007427; 311301; and 449586; PCT Application Nos. WO92/10736; WO91/14168; and WO91/06364. Other relevant patents in the viscometer art include U.S. Pat. Nos. 4,299,119; 3,435,665; and PCT Application No WO92/06365.

While the prior designs described principally involved suspension of a bob in a cantilevered manner from a single or multiple suspension points, one prior design has incorporaated suspension of the bob from a point removed from the fixation points for the torsion wire. In U.S. Pat. No. 2,796,758, the rotating cup 17 is specially constructed to have a U-shaped trough around its periphery. The torsion wire extends through the rotating cup and is fixed above and below the cup. The bob is, in turn, fixed to the torsion wire between the fixatiion points for the torsion wire. However, the readings of actual torsional displacement of the wire are taken adjacent the uppermost fixation point and not off the bob. A baseline system involving a target mounted to the bob for a neutral reading is used. Thereafter, a disc has to be physically rotated adjacent a fixation point until the indicator connected to the bob is again realigned with the target used to determine the initial position.

The apparatus of the present invention represents an improvement over the viscometer designs of the prior art, and, in particular, the Myers patent U.S. Pat No. 2,796,758. The apparatus of the present invention involves a use of a standard rotating cup, rather than a specially designed cup, as used in Myers. The apparatus of the present invention provides multiple fixation points for the torsion wire, coupled with a suspension point for the bob assembly unit between the fixation points. Both fixation points are aligned above the rotating cup so that standard cup geometries can be used. By fixing the bob as described, first order inaccuracies due to deflection from a swinging bob are eliminated. Instead, the bob becomes self-centering, producing deflection inaccuracies of only the second order. The apparatus of the present invention is more sensitive because it takes the readings of deflector closer to the mid-point of the wire and further from either points of fixation. The apparatus of the present invention takes a direct readout of the rotation of the torsion wire and, through the use of electronic transducers to determine the amount of twist, eliminates another factor of human error in relying on visible deflections read off of an adjacent scale. The apparatus of the present invention involves simple and quick change-out of bobs with minimal effects on accuracy due to such change-outs.

SUMMARY OF THE INVENTION

The invention comprises a viscometer which has a bob assembly unit suspended between the fixation points for a torsion wire. The torsion wire runs through a tube, which is connected to the bob. The tube has cutouts so that it may rotate in response to rotations of a cup, in which the bob is disposed. The framework that can include spokes or bars to support a fixation point for the wire is preferably positioned to extend through cutouts or open window-like slots in the tube so as not to interfere with rotational movements of the tube. An arm connected to the tube in conjunction with a transducer measures the angular deflection of the wire for determination of viscosity for the fluid being examined.

DETAILED DESCRIPTION OF THE PREFERRED EMBODIMENT

Figure 1:
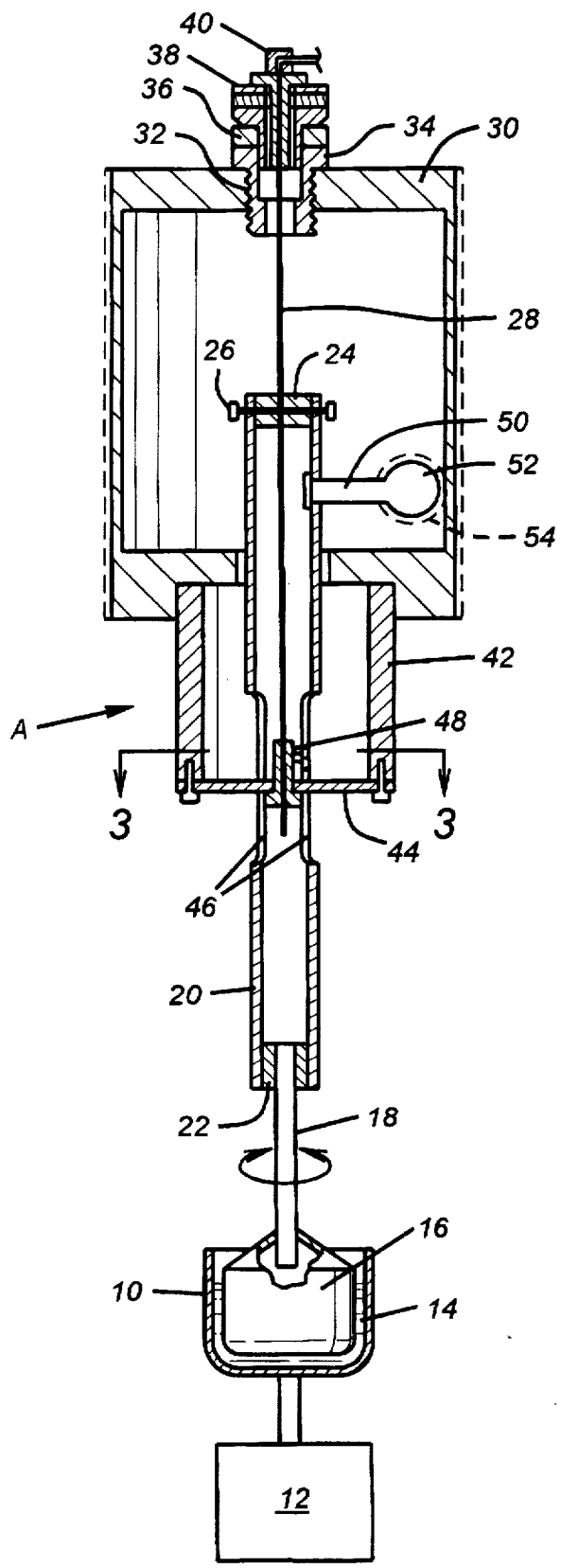
FIG. 1 is a schematic illustration of the apparatus and method of the present invention showing the assembly of the components and their relative positions.
Figure 2:
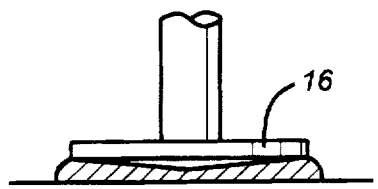
FIG. 2 is an alternate embodiment of the bob of the present invention using a tapered cone configuration for the bob.
Figure 3:
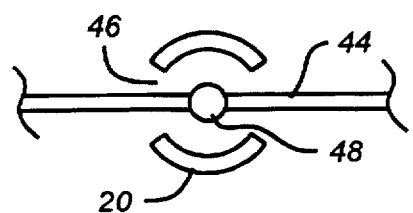
FIG. 3 is a section view along lines 3—3 of FIG. 1.

The apparats A is shown in FIG. 1. A container 10 is schematically shown as operably connected to a drive 12 which supports container 10 and rotates it a preselected speed. The container 10 may be of any desired volume and the preferred shape is cylindrical. A fluid 14 whose viscosity is to be determined is deposited in container 10. A bob 16 is positioned in the fluid 14 stored in container 10. As will be detailed below, the support assembly for the bob can be adjustable so as to allow insertion and extraction of bob 16 from a container 10. Alternatively, container 10 may be so situated with respect to drive 12, which could optionally include a rotary table, so as to allow positioning of the bob 16 within the container 10 by movement of container 10 or its underlying support structure, shown schematically as drive 12. In the preferred range, drive 12 can be a variable speed drive or a drive capable in other ways of delivering several preselected speeds preferably ranging in the order of about 0.01 RPM up to about 1000 RPM.

Bob 16 may be a cylinder shape or it can be a flat plate used in conjunction with a container 10 which itself can be another flat plate. Bob 16 may have a taper with 4° or less being preferred if such type of bob 16 is used. A cylinder shape is also preferred and can be of service for a wider variety of fluids.

Extending from bob 16 is shaft 18 which is preferably connected to a tube 20. Tube 20 moves in tandem with shaft 18 and bob 16. Shaft 18 is connected to tube 20 at its lower end 22. At upper end 24, a fixation device 26 is disposed for the purpose of fixing tube 20 to wire 28. Wire 28 is fixed in two points. The first point is on housing 30. Housing 30 has preferably a threaded bore 32 to which is mounted an adjustment nut 34. Above the adjustment nut 34 is a lock nut 36, which works in conjunction with a centralizer 38 to complete the upper attachment point of wire 28. Wire 28 has a projection 40 at its end which engages centralizer 38 to trap the upper end of wire 28. The lower end of wire 28 is fixed indirectly to housing 30. Housing 30 has a lower extension 42 characterized by a mounting bar 44. The mounting bar 44 extends through tube 20 through a slot 46. Mounted centrally on the mounting bar 44 is wire attachment 48. The attachment 48 can be any one of a variety of different mechanical attachments and is preferably releasable. The slots 46 are sufficiently wide to allow tube 20 to rotate along its longitudinal axis in response to a torque transmitted through the fluid 14 into bob assembly unit 16, resulting from drive 12 turning container 10. It is easy to see that the fixing point for the bob assembly unit 16 occurs between the upper fixation point at projection 40 and the lower attachment point at wire attachment 48. By turning the adjustment nut 34, the slackness in the wire 28 can be removed. The preferred material for wire 28 is a Phosphor Bronze Alloy with the thickness of the wire being dependent on the viscosity of the fluid being measured. Higher viscosity fluids allow for the use of thicker wires. For example, wire diameter ranges of 0.030"-0.850" can be used with anticipated viscosities of the drilling fluids (10 centipoise (cp)—1000 poise (p)). In the preferred embodiment, drive 12 can rotate container 10 at preselected speeds which can vary from as low as about 0.01 RPM to a maximum speed of in excess of 600 RPM. Rotation of container 10 resulting from operation of drive 12 induces a torque on the bob 16 which, in turn, induces tube 20 to rotate. Mounted to tube 20 close to the fixation point at the upper end 24 of tube 20 is arm 50 which, at its end, has transducer-sensing pad 52. Preferably an optical beam or acoustical transducer schematically shown as 54 senses the amount of movement of sensing pad or target 52 so that the measurement of angular deflection can be determined electronically.

In view of the techniques for mounting the bob 16, it can readily been seen that bobs can quickly be replaced or that the wire 28 can be replaced as needed, to accommodate testing of fluids of different viscosities.

Significantly, to improve sensitivity, the fixation point for bob 16 to the wire 28 occurs between the ends of wire 28. In the preferred embodiment, the fixation point at the upper end 24 of tube 20 occurs about midway on wire 28 between attachment 48 and projection 40. Further, the take-off point for a deflection measurement is also adjacent the fixation point between the tube 20 and the wire 28. Again, this reduces measurement errors by increasing sensitivity since the deflection is measured at a point on the wire that is most likely to twist correspondingly to the amount of applied toque from the fluid 14 onto bob 16, resulting from rotation of container 10 by drive 12. Through the use of electronic transducers, the precise movement of target 52 is determined electronically, thus further reducing human errors inherent in some of the prior designs by not requiring manual contact, visual observation, position judgement or any other interaction by a test operator.

The apparatus of the present invention facilitates use of standardized containers 10 and does not require complex containers, such as those disclosed in U.S. Pat. No. 2,796,758, which has a fixation point for the wire below its rotating container. In the apparatus of the present design, a readout of the amount of twist of tube 20 is made directly and through a transducer further eliminating errors due to indirect measurements, such as those employed in U.S. Pat. No. 2,796,758.

Since the wire 28 can be tensioned between two points, it is in efffect centralized. This eliminates the need as in the prior designs for relying on very thin wires and heavy bobs to keep the bob centered in the sample when the cap holding the sample is being rotated.

The mounting method illustrated in FIG. 1 also lends itself to great linearity in a broader range of speed than those devices of the prior art where linearity was particularly problematic at low speeds. The drive 12 could also be arranged to be sinusoidal in order to provide true gel characteristics of the sample. Sinusoidal drive involves a continuous change of direction at a predetermined speed after rotation of a particular distance. This back and forth action is especially useful with sensitive fluids when continuous rotation in a single direction can affect the fluid properties.

The use of the mounting system, as illustrated in FIG. 1, for the wire 28 also allows use of lower clearances between bob 16 and the container 10. Sample volumes can be reduced and measuring is improved accuracy through the use of a lower clearance made possible by the mounting method which effectively centralizes bob 16. The apparatus of the present invention makes it possible to achieve a ratio of bob to cup diameter of 0.96 or greater. In prior designs, this has been a problem due to lack of a centralizing effect on the bob found in prior designs.

The foregoing disclosure and description of the invention are illustrative and explanatory thereof, and various changes in the size, shape and materials, as well as in the detail of the illustrated construction, may be made without departing from the spirit of the invention.

I claim:

1. A viscometer, comprising:

a housing;

an elongated support wire connected to said housing in at least two mounting points;

a bob, said bob mounted to said wire at a point of fixation between said mounting points;

a container for a sample fluid to be viscosity tested;

a rotating mechanism acting on said container, with the fluid in said container in contact with said bob;

a measurement device to measure fluid viscosity by directly sensing, without requiring any manual contact, visual observation or judgement by a test operator, angular displacement of said wire adjacent said point of fixation of said bob responsive to a torque applied to said bob from the fluid.

2. The viscometer of claim 1, wherein:

said support wire is connected to said housing at an upper and a lower mounting point, both disposed on the same side of said container.

3. The viscometer of claim 2, wherein:

said bob further comprises an elongated extension spanning over said lower mounting point;

said extension connected to said support wire at said point of fixation for support of said bob by a fixation device;

said extension rotatable with respect to said lower mounting point of wire without contact therewith.

4. The viscometer of claim 3, wherein:

said extension of said bob is mounted to said wire at a point of fixation about midway between said upper and lower mounting points.

5. The viscometer of claim 4, further comprising:

mechanical adjustment on at least one of said mounting points for said wire for adjusting slack out of said wire.

6. The viscometer of claim 3, wherein:

said measurement device is disposed on said extension of said bob close to its said point of fixation to said support wire.

7. A method of measuring viscosity of a fluid, comprising:

placing the fluid in a container;

rotating the container with the fluid in it;

placing a bob in the container;

supporting said bob from a wire attached at upper and lower mounting points to a viscometer housing above the container, wherein said bob is secured to said wire at a fixation point disposed between said points;

sensing with an instrument rotational movement of the bob directly and without requiring any manual contact, visual observation or judgement by a test operator of said bob, responsive to an applied torque from the fluid rotating with said container.

8. The method of claim 7, further comprising the step of:

supporting said bob about midway between said two points.

9. The method of claim 8 or 7, further comprising:

mounting an extension tube having a plurality of cutouts thereon to said bob;

securing said bob to said wire by attachment of said extension tube to said wire;

supporting one of two said mounting points for said wire within said extension tube relative to said viscometer housing by means of two or more support members connecting said wire with said housing;

providing unobstructed passage of two or more support members on a housing to pass to said mounting point in said extension.

10. The method of claim 9, wherein said sensing further comprises:

attaching an arm to said extension tube having a target thereon;

aiming said instrument which further comprises a transducer having a position-sensitive device at said target to detect the amount of its movement.

11. The method of claim 7, 8, or 10, further comprising:

providing an adjustment mechanism on at least one of said mounting points to allow removal of slack from said wire.

12. A viscometer, comprising:

a housing;

an elongated support wire connected to said housing in at least two mounting points;

a bob, said bob mounted to said wire at a point of fixation between said mounting points;

a container for a sample fluid to be viscosity tested;

a rotating mechanism acting on said container, with the fluid in said container in contact with said bob;

a measurement device to measure viscosity by sensing angular displacement responsive to a torque applied to said bob from the fluid;

said support wire is connected to said housing at an upper and a lower mounting point, both disposed on the same side of said container;

said bob further comprises an elongated extension spanning over said lower mounting point;

said extension connected to said support wire at said point of fixation for support of said bob by a fixation device;

said extension rotatable with respect to said lower mounting point of wire without contact therewith;

said housing comprises a plurality of spokes to support said lower mounting point;

said extension comprising a plurality of cutouts, each said spoke extending through a corresponding said cutout to allow said bob rotational freedom with respect to said housing, which remains fixed.

13. The viscometer of claim 3, wherein said measurement device further comprises:

an arm extending from said extension;

a sensor for detecting angular movement of said arm responsive to torque applied to said bob from the fluid being tested during rotation of said container.

14. The viscometer of claim 12, wherein said measurement device further comprises:

an arm extending from said extension;

a sensor for detecting angular movement of said arm responsive to torque applied to said bob from the fluid being tested during rotation of said container.

15. The viscometer of claim 14, wherein:

said arm extends radially from said extension and further comprises a target, said sensor disposed adjacent said target for determination of the amount of movement of said target.

16. A viscometer, comprising:

a housing;

an elongated support wire connected to said housing in at least two mounting points;

a bob, said bob mounted to said wire at a point of fixation between said mounting points;

a container for a sample fluid to be viscosity tested;

a rotating mechanism acting on said container, with the fluid therein in contact with said bob;

a measurement device to measure fluid viscosity by directly sensing, without requiring any manual contact, visual observation or judgement by a test operator, angular displacement of said wire adjacent said point of fixation of said bob responsive to a torque applied to said bob from the fluid;

said means for rotation can vary the speed of said container between about 0.01 RPM to about 1000 RPM.

17. A viscometer, comprising:

a housing;

an elongated support wire connected to said housing in at least two mounting points;

a bob, said bob mounted to said wire at a point of fixation between said mounting points;

a container for a sample fluid to be viscosity tested;

a rotating mechanism acting on said container, with the fluid therein in contact with said bob;

a measurement device to measure fluid viscosity by directly sensing, without requiring any manual contact, visual observation or judgement by a test operator, angular displacement of said wire adjacent said point of fixation of said bob responsive to a torque applied to said bob from the fluid;

the ratio of diameters of said bob to said container is about 0.96 or greater.

18. A viscometer, comprising:

a housing;

an elongated support wire connected to said housing in at least two mounting points;

a bob, said bob mounted to said wire at a point of fixation between said mounting points;

a container for a sample fluid to be viscosity tested;

a rotating mechanism acting on said container, with the fluid therein in contact with said bob;

a measurement device to measure fluid viscosity by directly sensing, without requiring any manual contact, visual observation or judgement by a test operator, angular displacement of said wire adjacent said point of fixation of said bob responsive to a torque applied to said bob from the fluid;

said container and said bob are substantially flat with said bob having an inclined surface varying up to about a 4° taper.

19. A method of measuring viscosity of a fluid, comprising:

placing the fluid in a container;

rotating the container with the fluid in it;

placing a bob in the container;

supporting said bob from a wire attached at an upper and a lower mounting points to a viscometer housing above the container, wherein said bob is secured to said wire at a fixation point disposed between said points;

sensing rotational movement of the bob directly, responsive to an applied torque from the fluid rotating with said container;

said placing step comprises using a substantially flat surface and a bob having an inclined surface which varies up to about a 4° taper.

20. A method of measuring viscosity of a fluid, comprising:

placing the fluid in a container;

rotating the container with the fluid in it;

placing a bob in the container;

supporting said bob from a wire attached at an upper and a lower mounting points to a viscometer housing above the container, wherein said bob is secured to said wire at a fixation point disposed between said points;

sensing rotational movement of the bob directly, responsive to an applied torque from the fluid rotating with said container;

mounting an extension tube having a plurality of cutouts thereon to said bob;.

securing said bob to said wire by attaching at said extension tube;

supporting one of two said mounting points for said wire within said extension tube relative to said viscometer housing by means of two or more support members connecting said wire with said housing;

providing unobstructed passage of two or more support members on a housing to pass to said mounting point in said extension;

said placing step comprises using a substantially flat surface and a bob having an inclined surface which varies up to about a 4° taper.

* * * * *